(12) United States Patent
Baker

(10) Patent No.: US 7,608,052 B1
(45) Date of Patent: *Oct. 27, 2009

(54) CERVICAL BRACE AND THERAPY DEVICE

(76) Inventor: Ford S. Baker, 25145 Bickham Rd., Jackson, LA (US) 70748

( * ) Notice: Subject to any disclaimer, the term of this patent is extended or adjusted under 35 U.S.C. 154(b) by 244 days.

This patent is subject to a terminal disclaimer.

(21) Appl. No.: 11/732,877

(22) Filed: Apr. 5, 2007

Related U.S. Application Data

(63) Continuation-in-part of application No. 10/915,183, filed on Aug. 10, 2004, now Pat. No. 7,371,221.

(51) Int. Cl.
*A61F 5/00* (2006.01)
(52) U.S. Cl. .................. 602/18; 128/DIG. 23
(58) Field of Classification Search ............. 602/17–19; 128/DIG. 23
See application file for complete search history.

(56) References Cited

U.S. PATENT DOCUMENTS

| | | | |
|---|---|---|---|
| 2,474,200 A * | 6/1949 | McBee ................. 602/18 |
| 3,724,452 A | 4/1973 | Nitschke |
| 4,204,529 A | 5/1980 | Cochrane |
| 4,520,801 A | 6/1985 | Lerman |
| 4,712,540 A | 12/1987 | Tucker et al. |
| 4,988,093 A | 1/1991 | Forrest et al. |
| 5,097,824 A | 3/1992 | Garth |
| 5,116,359 A | 5/1992 | Moore |
| 5,320,640 A | 6/1994 | Riddle et al. |
| 5,336,138 A | 8/1994 | Arjawat |
| 5,360,383 A | 11/1994 | Boren |
| 5,531,669 A | 7/1996 | Varnau |
| 5,575,763 A | 11/1996 | Nagata et al. |
| 5,964,722 A | 10/1999 | Goralnik et al. |
| 5,984,836 A | 11/1999 | Casali |
| 5,997,440 A | 12/1999 | Hanoun |
| 6,106,437 A | 8/2000 | Brooks |
| 6,458,090 B1 | 10/2002 | Walpin |
| 6,551,214 B1 | 4/2003 | Taimela |
| 6,599,257 B2 | 7/2003 | Al-Obaidi et al. |
| 6,692,451 B2 | 2/2004 | Splane, Jr. |

\* cited by examiner

*Primary Examiner*—Michael A. Brown
(74) *Attorney, Agent, or Firm*—Roy, Kiesel, etc.

(57) ABSTRACT

A cervical brace and therapy device for use to rehabilitate an injured neck of a person is described having a base support structure shaped to fit about the neck and rest on the shoulders of the person; a support ring assembly attachable to the base support structure in a horizontal position below the mandible of the person, the support ring assembly having an anterior section and a posterior section; a rotational member attached to the support ring assembly in a manner to rotate about the support ring assembly; an occipital-mandible support member shaped to accommodate the mandible and the occipital portions of the head of the person, the occipital-mandible support member being attachable to the rotational member in a manner to permit the occipital-mandible support member a predetermined range of rotation; and a cushioning assembly situated within the support ring assembly to cushion against an abrupt stop at the end of the predetermined range of motion.

28 Claims, 7 Drawing Sheets

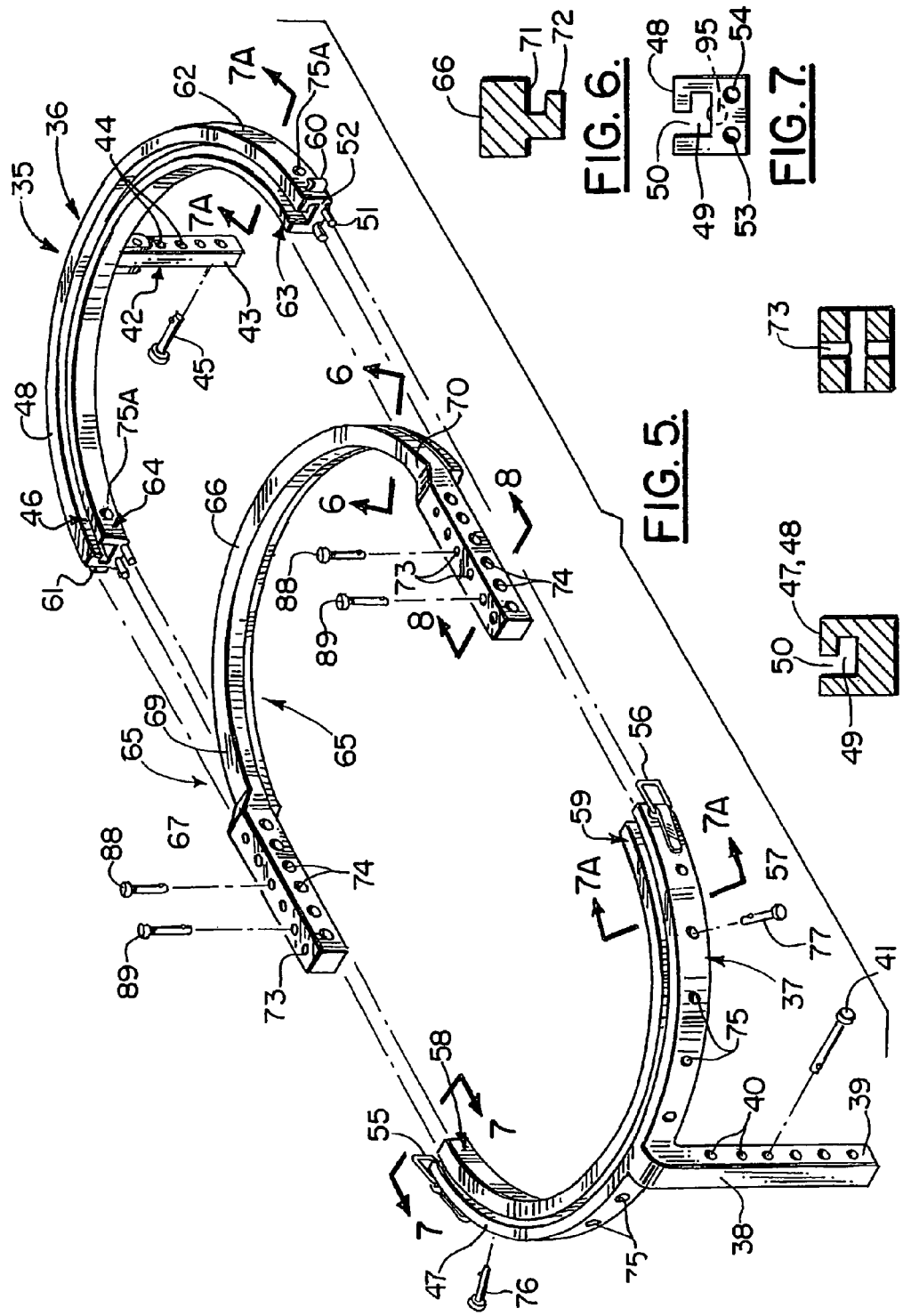

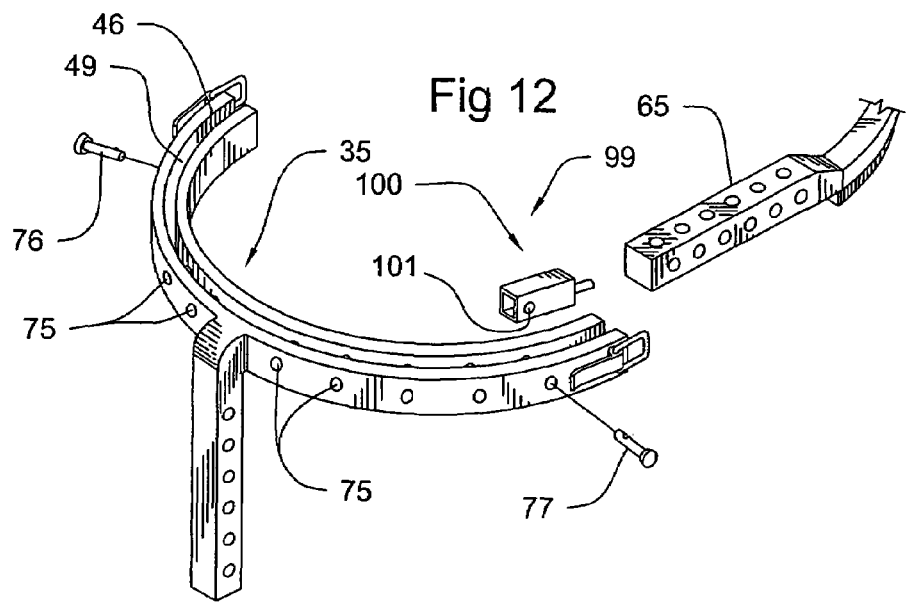
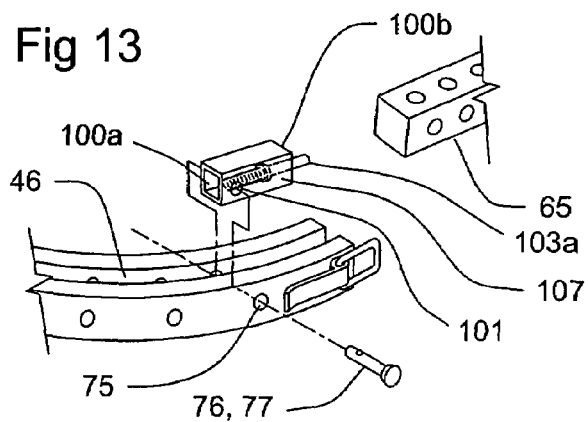
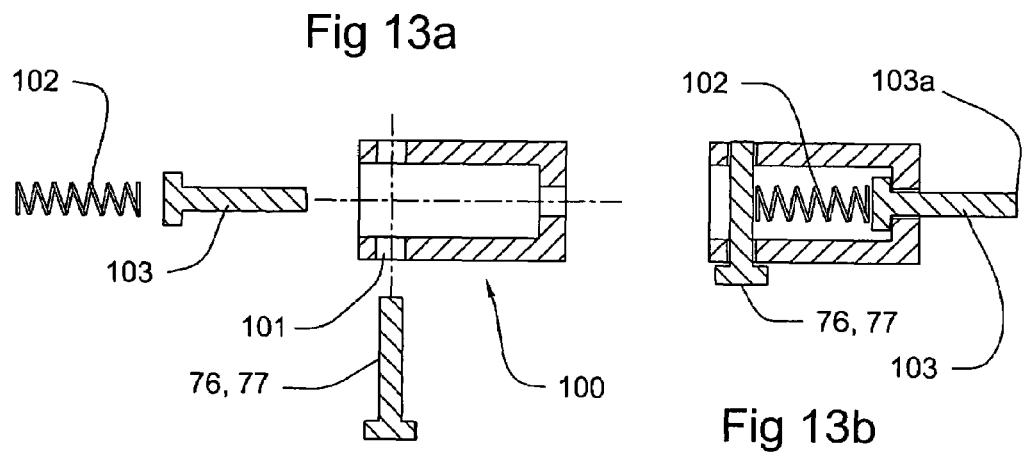

CERVICAL BRACE AND THERAPY DEVICE

CROSS-REFERENCE TO RELATED APPLICATIONS

This application is a continuation in part of U.S. patent application Ser. No. 10/915,183 filed Aug. 10, 2004, now U.S. Pat. No. 7,371,221 which is hereby incorporated by reference in its entirety.

FIELD OF THE INVENTION

The present invention pertains to the field of orthopedic devices, and more particularly to cervical brace and therapy devices for the head and neck.

BACKGROUND FOR THE INVENTION

Safely supporting the head and strengthening muscles of the neck following cervical spine or cervical-thoracic spine injuries is a delicate rehabilitative process. The anatomical region involved includes the occipital-cervical junction, cervicothoracic junction, cervical vertebrae, the upper thoracic vertebrae and all of the associated muscles, ligaments, tendons and other connective tissues in these regions.

The prior art includes numerous cervical orthoses designed to partially or totally immobilize the head and neck. Examples of such orthoses are described in U.S. Pat. No. 4,204,529 to Crochrane; U.S. Pat. No. 4,520,801 to Lerman; U.S. Pat. No. 4,712,540 to Tucker; U.S. Pat. No. 5,097,824 to Garth; U.S. Pat. No. 5,575,763 to Nagata et al. The immobilization provided by these devices result in a desired spinal alignment, reduced neck muscle strain or spasm and transfer the load of the head to the shoulder area. However, these cervical orthoses create the problem of extended immobilization weakening the muscles that stabilize the head and neck. They do not permit the rotation of the head, which may result in further injury to the patient.

Another example of the prior art is illustrated in U.S. Pat. No. 6,458,090 to Walpin. The multi-positional support device disclosed allows for support in various fixed degrees of rotation as well as small ranges of head and neck rotation. However, this device presents the problem of small ranges of head and neck rotation insufficiently exercising atrophied neck muscles to strengthen them to safely support the load of the head and allow extensive ranges of rotation of the head.

Other known cervical therapy devices, such as described in U.S. Pat. No. 5,116,359 to Moore; U.S. Pat. No. 5,320,640 to Riddle et al; U.S. Pat. No. 5,336,138 to Arjawat; U.S. Pat. No. 6,551,214 to Taimela; U.S. Pat. No. 6,599,257 to Al-Obaidi et al; and U.S. Pat. No. 6,692,451 to Splane, support the head and therapeutically exercise the neck in one or more planes. However, these cervical therapy devices are cumbersome cervical therapy devices built onto a chair or table requiring patients to visit a physical therapy facility for cervical therapy.

Known neck exercise devices. such as described in U.S. Pat. No. 4,988,093 to Forrest et al; U.S. Pat. No. 5,360,383 to Boren; U.S. Pat. No. 5,984,836 to Casali; U.S. Pat. No. 5,997,440 to Hanoun; and U.S. Pat. No. 6,106,437 to Brooks, usually include a head harness or helmet of various types and resistive forces. Such exercise devices are designed to strengthen neck muscles without supporting the cervical spine and without transferring the load of the head to the shoulders. This lack of support, load transfer and use of resistive forces risk injury to patients with muscles atrophied from immobilization and insufficient strength to safely support and rotate the head against resistive forces.

Therefore, one object of this invention is to provide an adjustable device wearable during the activities of daily living that comfortably supports the cervical and upper thoracic spine. Those learned in the art recognize the importance of strengthening atrophied neck muscles in one plane of motion at a time thus reducing the risk of injury to patients.

Another object of this invention is to provide a support and therapy device that comfortably transfers the load of the head to the shoulders and upper chest of the patient.

Still another object of this invention is to provide a support and therapy device that allows the neck muscles to strengthen with successive extensive ranges of active rotation in the horizontal plane without tilting the head.

A further object of this invention is to provide a wearable, adjustable cervical orthosis that facilitates a method of cervical therapy where the head actively rotates in successive extensive ranges of horizontal rotation without tilting.

A still further object of this invention is to provide a support and therapy device having support and therapy functions that safely strengthen muscles responsible for head rotation that have atrophied by immobilization in known cervical support devices or as a result of neuromuscular disease thus permitting safe increases in the range of head rotation during treatment.

Another object of this invention is to provide a cost effective support and therapy device.

These and other objects and advantages of this invention shall become apparent from the ensuing descriptions of the invention.

SUMMARY OF THE INVENTION

The cervical brace and therapy device for use to rehabilitate an injured neck of a person is constructed having a base support structure shaped to fit about the neck and rest on the shoulders of the person. Attachable to the base support structure is a support ring assembly. The support ring assembly is attached to be in a horizontal position below the mandible of the person. Attached to the support ring assembly is a rotational member. The attachment is done in a manner to permit the rotational member to rotate about the support ring assembly in a predetermined range of horizontal rotation. In addition there is an occipital-mandible support member shaped to accommodate the mandible and the occipital portions of the head of the person. The occipital-mandible support member being attachable to the rotational member in a manner to permit the occipital-mandible support member to rotate up to the predetermined range of horizontal rotation.

BRIEF DESCRIPTION OF THE DRAWINGS

FIG. 5 is an exploded view illustrating the connectivity of the anterior and posterior support ring assembly members with the arcuate rotational member of the preferred embodiment of FIG. 1.

FIG. 6 is an end view taken along lines 6-6 of FIG. 5.

FIG. 7 is a cross-sectional view taken along lines 7-7 of FIG. 5.

FIG. 7A is a cross-sectional view taken along lines 7A-7A of FIG. 5.

FIG. 8 is a cross-sectional view taken along lines 8-8 of FIG. 5.

FIG. 12 is an exploded view illustrating the positioning of the cushioning assembly within the channel of the track of the posterior support ring assembly member.

FIG. 13 is a three-dimensional partially exploded view of a preferred embodiment of the housing of the cushioning assembly.

FIGS. 13A and 13B are cross-sectional side views of a preferred embodiment of the housing of the cushioning assembly.

DETAILED DESCRIPTION OF THE INVENTION

Figure 1:
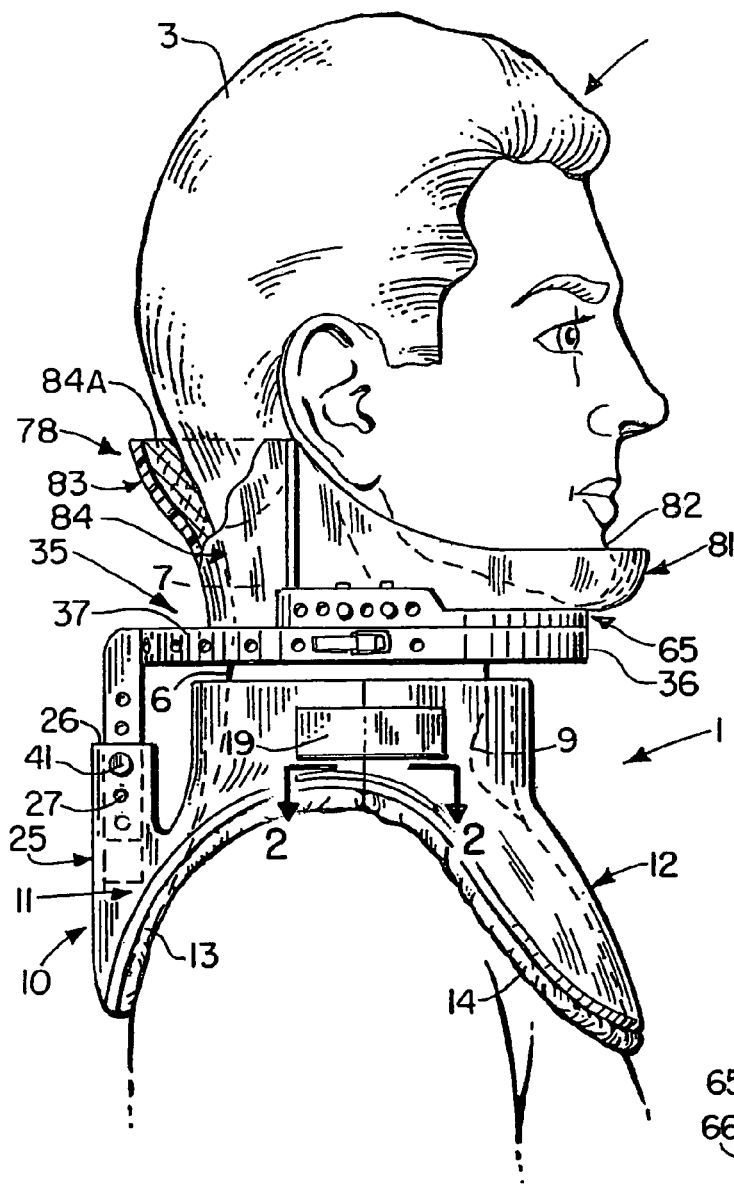
FIG. 1 is a side view of one preferred embodiment of the cervical brace and cervical therapy device positioned on the patient.

Without attempting to limit the scope of the invention, the preferred embodiments of the invention are described with reference to FIGS. 1-10.

As seen in FIGS. 1-4, the cervical brace and therapy device 1 is positioned for use on the patient 2 being treated for a neck injury. The device 1 comprises four basic elements: a base support structure 10, a support ring assembly 35, a rotational member 65 and an occipital-mandible support member 78.

The function of the base support structure 10 is to provide a stable platform for transferring the load or weight of the patient head 3 principally to the patient left and right shoulders 4 and 5, respectively, and to a lesser extent to the back side 6 of the patient neck 7, the patient upper back 8, and the patient sternum area 9. In one of its preferred embodiments base support structure 10 include a rear neck contoured plate 11 and a front neck-sternum plate 12. Both plates 11 and 12 are molded from a thermoset plastic or resin and shaped to conform generally to rest on shoulders 4 and 5, patient back side 6 of the neck and patient upper back 8. If desired, plates 11 and 12 could be constructed to extend further down the patient's chest and back to reduce flexion and extension of the neck. One such alternate construction would be extension plates attachable to plates 11 and 12 respectively. Each plate is also provided with a cushioning pad 13 and 14, respectively, that is attached to the interior surface walls 15 and 16, respectively, to provide cushioning of the load on shoulders 4 and 5. Once plates 11 and 12 are positioned on the shoulders 4 and 5, respectively, they are attached to one another by fastening means 17, 18, 19 and 20 located on the shoulder section 21 and neck section 22 of plates 11 and 12, respectively. A preferred fastening means is a conventional hook and loop fastener; although other known fasteners such as latch assemblies, snaps, cinches or combinations of these can be used. In an alternative embodiment straps 97 (see FIG. 1) attached to plates 11 and 12 would go around the upper torso and underneath the arms to provide additional stabilization to plates 11 and 12 and immobilization of the head.

Figure 2:
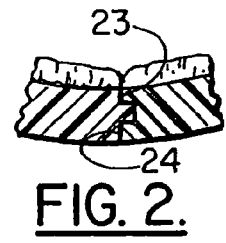
FIG. 2 is a cross-sectional view taken along lines 2-2 of FIG. 1.
Figure 3:
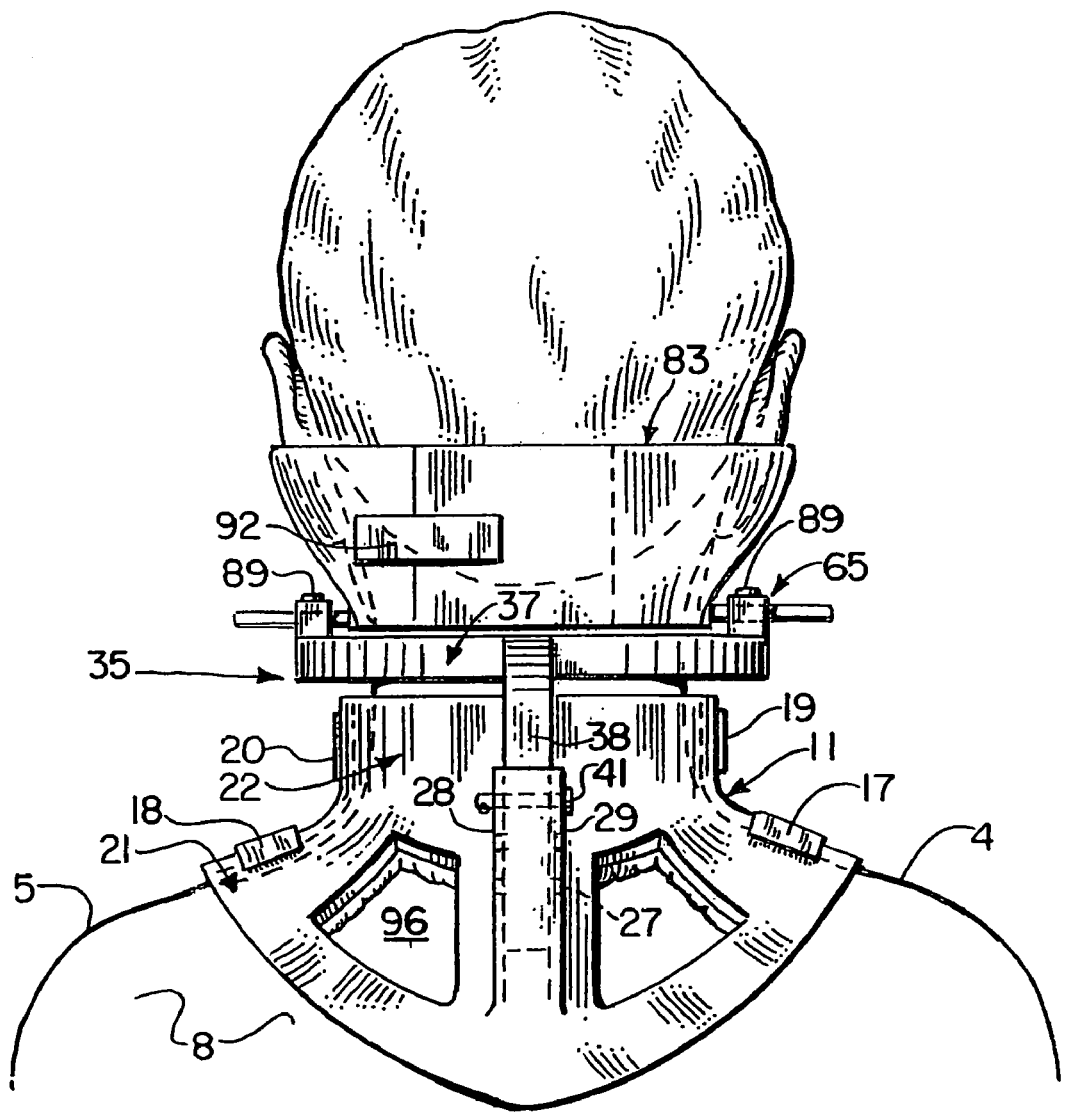
FIG. 3 is a back view of the preferred embodiment of FIG. 1 positioned on the patient.
Figure 4:
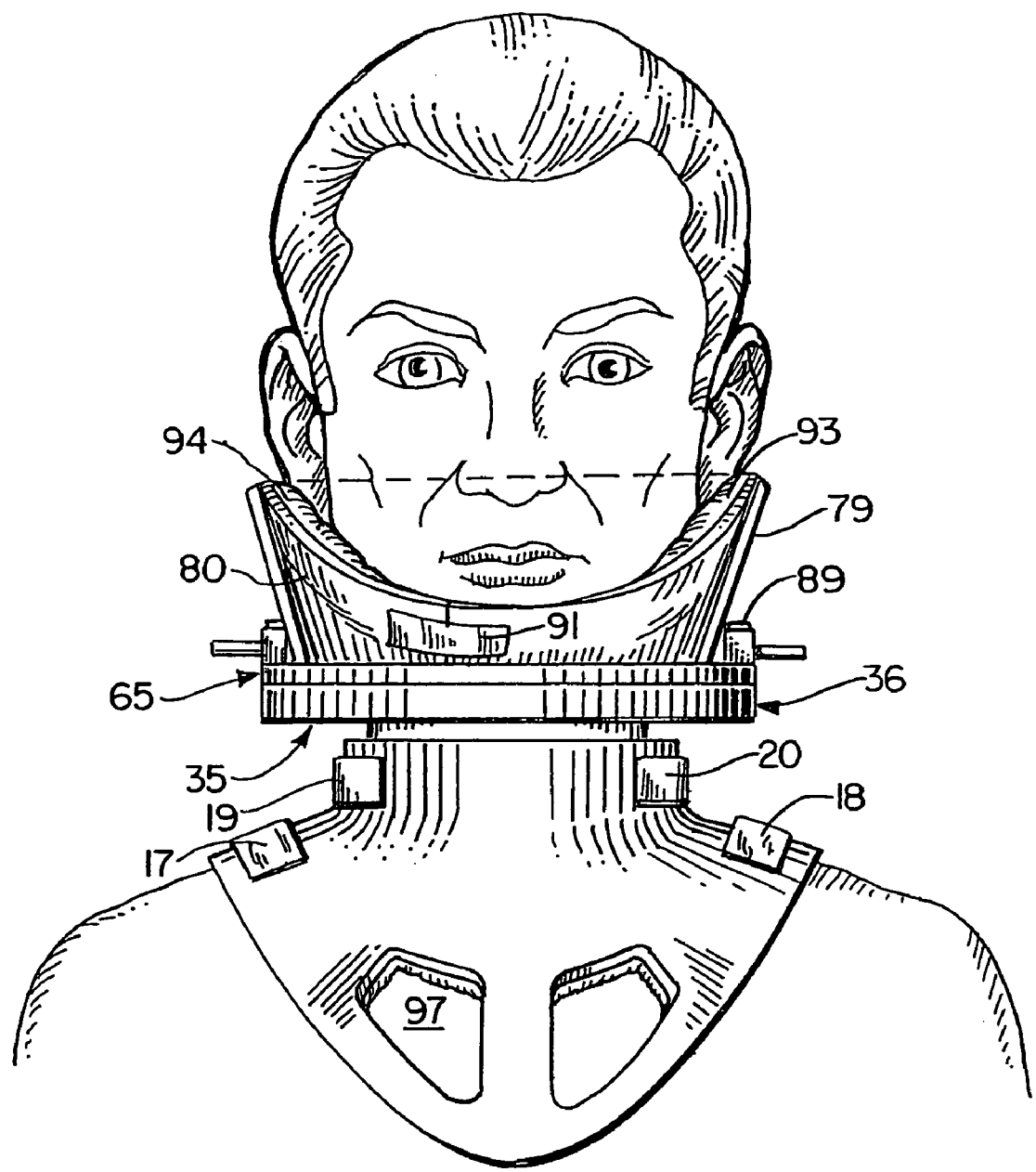
FIG. 4 is a front view of the preferred embodiment of FIG. 1 positioned on the patient.

As illustrated in FIG. 2, in a preferred embodiment the abutting edges 23 and 24 of plates 11 and 12 are constructed in a mating tongue-and-groove design to facilitate alignment of the two plates, as well provide for a more stable platform for the load or weight transfer from the head 3 to the shoulders 4 and 5. Other known interlocking or overlapping joint designs can be employed. In another preferred embodiment as illustrated in FIGS. 3 and 4, plates 11 and 12 do not need to be solid, but can be constructed having open areas 96 and 97, respectively, to reduce their weight, better ventilate the body heat, and increase wearing comfort.

Plate 11 is provided with a vertically extending tubular member 25 constructed from a hard plastic or other similar material to provide rigidity to the member. Tubular member 25 is constructed having a central cavity 26. A series of aligned openings 27 are provided in the opposite side walls 28 and 29 of tubular member 25 to position support ring assembly 35 in its desired position as discussed below.

Figure 1B:
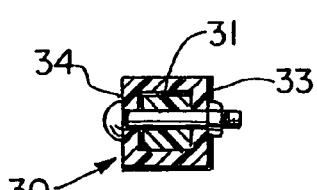
FIG. 1B is a cross-sectional view taken along lines 1B-1B of FIG. 1A.
Figure 1A:
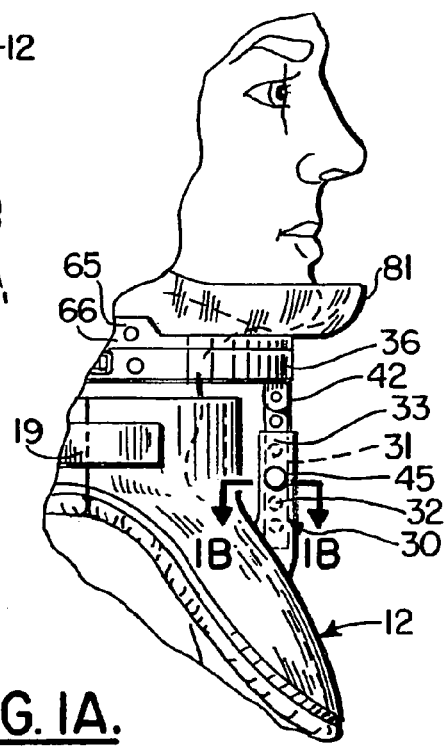
FIG. 1A is a partial side view of an alternative embodiment similar to FIG. 1, but wherein an anterior support strut is utilized to better maintain the support ring assembly in a horizontal position.

In a more preferred embodiment illustrated in FIG. 1A and FIG. 1B, plate 12 is provided with a vertically extending tubular member 30 also constructed from a hard plastic or other similar material to provide rigidity to the member. The tubular member 30 is constructed having a tubular central cavity 31. A series of aligned openings 32 are provided in the opposite side walls 33 and 34 of tubular member 30. In this embodiment support ring assembly 35 will be more securely held in the desired horizontal position and be more able to prevent the patient head from tilting which may cause further injury to the neck.

Referring now to FIGS. 4-8 a preferred embodiment of support ring assembly 35 and rotational member 65 are illustrated. Support ring assembly 35 comprises an anterior section 36 and a posterior section 37. In a preferred embodiment anterior section 36 and posterior section 37 will form a circle when joined together. The posterior section 37 is provided with a vertically downwardly extending bar 38 having a cross-section similar in shape but slightly smaller than the cross-section of central cavity 26 to permit the lower end 39 of bar 38 to be positioned in central cavity 26. Bar 38 is provided with a series of vertically aligned openings 40 extending through bar 38. The height of support ring assembly 35 can be adjusted by moving bar 38 vertically up and down in central cavity and fixed at the desired height by inserting a locking pin 41 through one pair of aligned openings 27 and one of openings 40 (see also FIG. 1). The locking pin 41 can be selected from any number of well known structures that can be used to secure the alignment. Examples include cotter pins, bolts, screws (if the openings are threaded), etc.

In a preferred embodiment the anterior section 36 is also provided with a vertically downward extending bar 42 having a cross-section similar in shape, but slightly smaller than the cross-section of central cavity 31 to permit the lower end 43 of bar 42 to be positioned in central cavity 31 (see also FIG. 1A). Bar 42 is also provided with a series of vertically aligned openings 44 extending through bar 42. As with bar 38 the height of support ring assembly 35 can be fixed at the desired height by inserting a locking pin 45 through on pair of aligned openings 32 and one of openings 44. In a more preferred embodiment the positioning of bar openings 44 and tubular member openings 32 are such that they are horizontally aligned with corresponding bar openings 32 and tubular member openings 27, respectively. This configuration facilitates assembly of device 1 and more achieves a more level positioning of support ring assembly 35.

Both anterior section 36 and posterior section 37 have a track 46 located on their upper surfaces 47 and 48, respectively. The purpose of track 46 is to provide a path of known position and dimensions along which rotational member 65 can slide. The cross-sectional configuration of track 46 can take any of the many known shapes that are known to serve the desired purpose. A particular cross-sectional configuration is illustrated in FIG. 7. In this configuration track 46 of anterior section 36 is an "L-shaped" channel 49 having its upper end 50 opening in upper surface 48. Posterior section 37 is provided with a similarly shaped channel 49. In an alternative embodiment illustrated in FIG. 7 recessed ball bearings 95 may be placed in channel 49 to decrease resistance of the sliding rotational member 65.

In a preferred embodiment both anterior section 36 and posterior section 37 will have alignment means located on the abutting ends of the two sections to facilitate proper joining and formation of a continuous circular track 46. One such alignment means can include pins 51 protruding from end surface 52 of anterior section 36 that can be extended into corresponding openings 53 in end surface 54 of posterior section 37. Openings 53 are shaped to permit pins 51 to extend completely into openings 53 but of a cross-sectional shape to permit a snug fit. Latches 55 and 56 are positioned on outer side wall 57 at the opposing end sections 58 and 59 of the posterior section 37 with catches 60 and 61 affixed on the outer side wall 62 at the opposing end sections 63 and 64 of anterior section 36.

As is illustrated in FIGS. 4-8, rotational member 65 includes a U-shaped tracking bar 66 with locking bars 67 and 68 extending from opposing ends 69 and 70, respectively, of tracking bar 66. Extending from the bottom surface 71 of tracking bar 66 is an L-shaped ridge 72 shaped and sized to fit in channel 49 to permit rotational member 65 to rotate when ridge 72 moves within channel 49. Each locking bar 67 and 68 is provided with a first series of openings 73 extending vertically through its respective bar and a second series of openings 74 extending horizontally through its respective bar.

To control the degree of rotation of tracking bar 66, posterior section 37 is provided with a series of horizontal openings 75 extending through channel 49 of section 37. These openings 75 are positioned at predetermined angles from the center of the circle formed by the joined sections 36 and 37. Pins 76 and 77 can be inserted through openings 75 to block channel 49 and thus limit the range of rotation that rotational member 65 can travel. In like fashion anterior section 36 can also be provided with a horizontal opening 75A extending through its channel 49A to restrict the travel of rotational member 65. In a preferred embodiment pins 76 and 77 are set to allow active rotational ranges of up to 60 degrees, up to 90 degrees, up to 120 degrees, up to 150 degrees, up to 180 degrees and up to 210 degrees. Numerous embodiments of the present invention are possible to allow multiple extensive ranges of horizontal rotation of the head without tilting. Thus, the present invention achieves the object of solving the cost effective need of a single device providing head and neck immobilization as well as furthering rehabilitation by safely strengthening muscles responsible for head rotation and increasing the range of said rotation.

In a more preferred embodiment of the invention, cervical brace and therapy device 1 is provided with a cushioning assembly 99 that can be variably positioned in track 46, anterior to desired locking pin or pins 76,77, to alert the patient of the nearing end of the predetermined range of motion and to provide a cushion against an abrupt or jerky stop. In this manner, the risk of injury to the patient is reduced. Cushioning assembly 99 is further advantageous in that it can also be utilized to progressively strengthen the neck muscles by providing a resistive force. In a preferred embodiment, cushioning assembly 99 comprises a hollow housing 100 designed and configured to be positioned within channel 49 of track 46 of support ring assembly 35. See FIGS. 12 and 13. Housing 100 further comprises a first end 100a that is completely open-ended and a second end that is partially open-ended 100b to allow yield member 103 to extend outwardly from the interior of housing 100, as further discussed below. Housing 100 further comprises a horizontal opening 101 extending through a side plate 107 of housing 100, this opening 101 designed to be in alignment with a user-selected horizontal channel opening 75, when housing 100 is slid and positioned within channel 49, as will be further discussed below. As depicted by FIGS. 13A and 13B, housing 100 further comprises a cushioning member 102, such as a coil, spring, or the like, running the length of housing 100 from first end 100a to second end 100b, cushioning member 102 further being affixed to a yield member 103 situated in second end 100b of housing 100. As depicted by FIGS. 13 and 13B, a portion 103a of yield member 103 extends outwardly from the interior of housing 100 at second end of housing 100b, this portion 103a of yield member 103 to be engaged by rotational member 65, as will be further discussed below. In operation, housing 100 will first be positioned within channel 49 of track 46 such that horizontal opening 101 of housing 100 is in parallel alignment with a user-selected horizontal channel opening 75 extending through track 46 and corresponding to a pre-determined range of motion. See FIG. 12. Pin 76 or 77 will then be inserted into these aligned openings 75 and 101. In this fashion, pin 76 or 77 serves two purposes. First, it blocks channel 49 at the desired horizontal opening 75 to thus limit the range of rotation that rotational member 65 can travel. Second, by extending horizontally through opening 101 of housing 100, pin 76 or 77 secures cushioning member 102 within housing 100 and further locks housing 100 in channel 49. In operation, when the patient nears the end of the predetermined range of motion, approaching locking pin 76 or 77, the end of rotational member 65 will engage the portion 103a of yield member 103 that extends outwardly from second end of housing 100b, such that this portion 103a of yield member 103 is pushed inwardly toward housing 100 and against cushioning member 102. Cushioning member 102, preferably a spring, coil, or the like, in turn will become compressed, and check the movement of yield member 103 and rotational member 65 pushing against yield member 103, to thereby provide a cushion the end of travel of rotational member 65. In this fashion, a direct and abrupt contact of the rotational member 65 with locking pin 76 or 77 is avoided.

Figure 9:
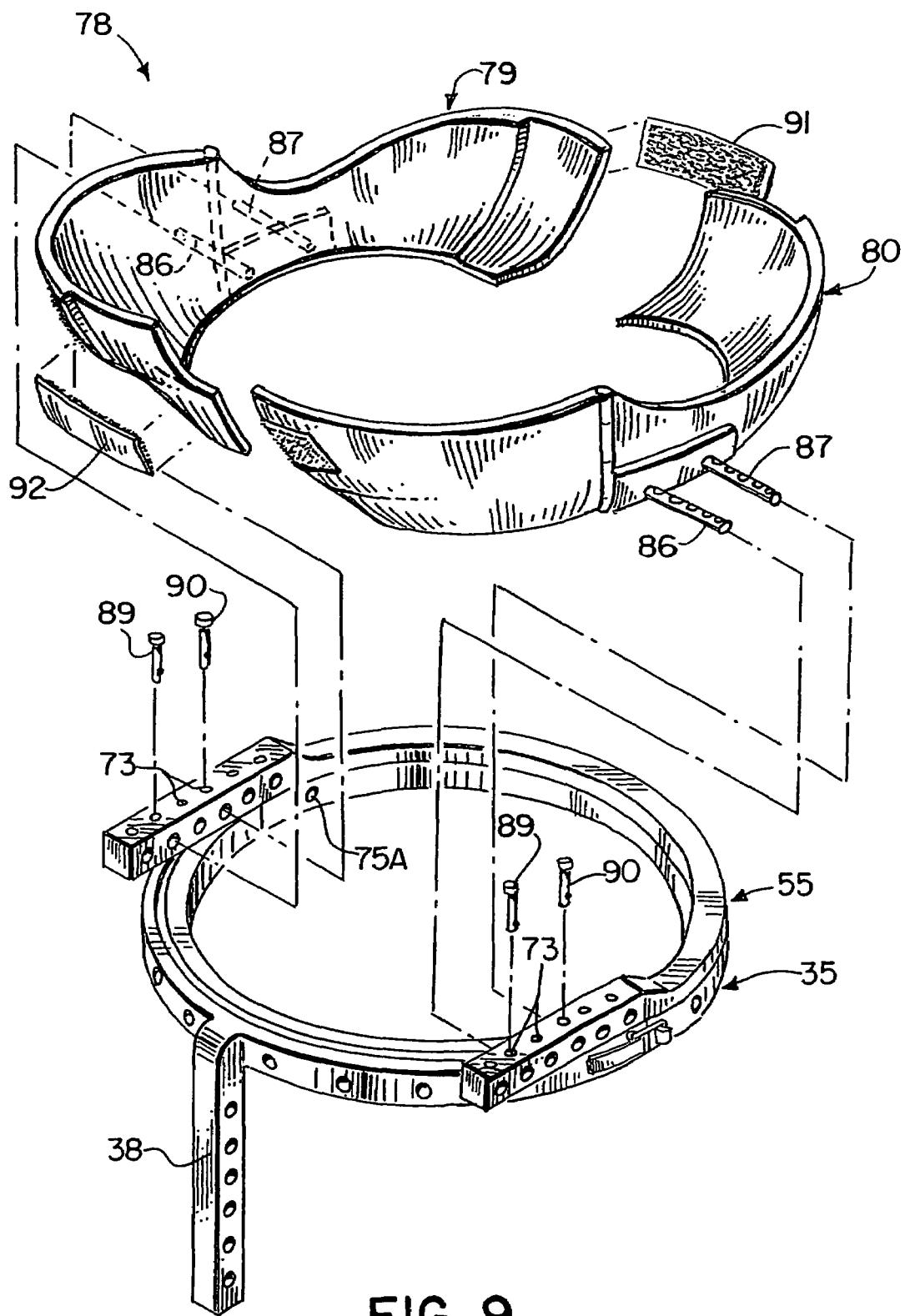
FIG. 9 is an exploded view illustrating the connectivity of left and right sections of the occipital-mandible support structure with the arcuate rotational member of the preferred embodiment of FIG. 1.
Figure 10:
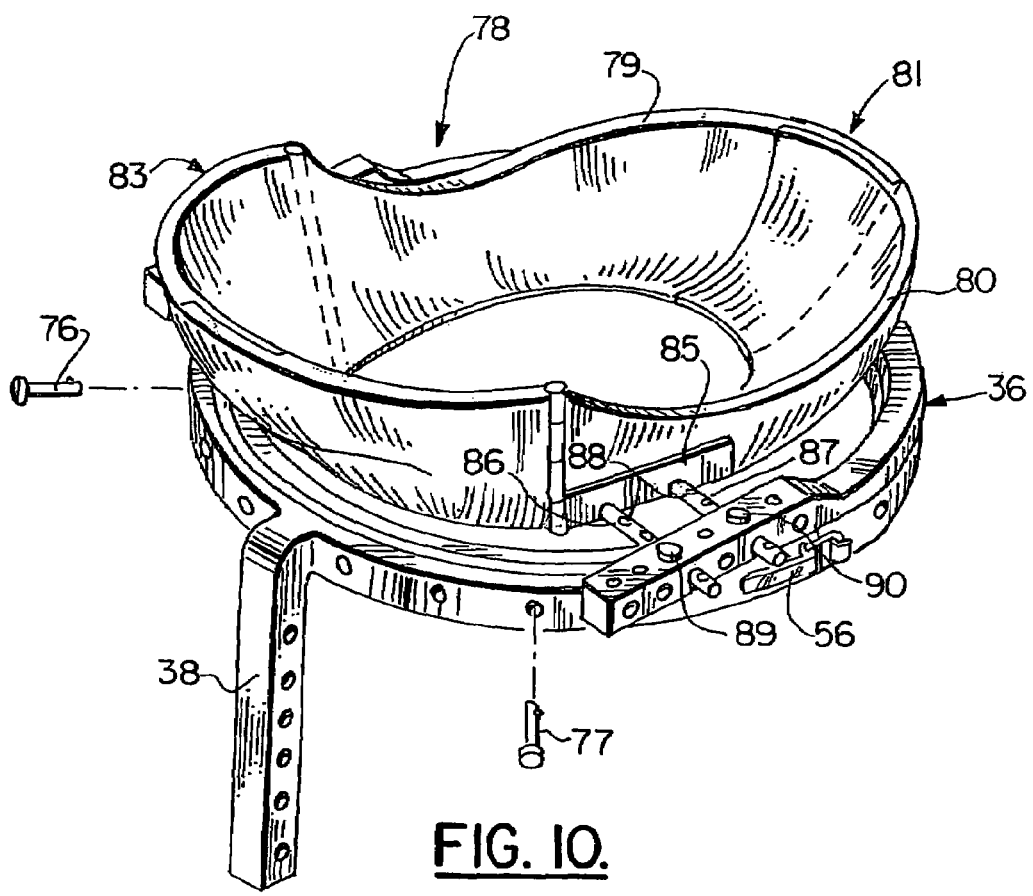
FIG. 10 is a three-quarter perspective view of the occipital-mandible support structure mounted on the rotational member of the preferred embodiment of FIG. 1.
Figure 11:
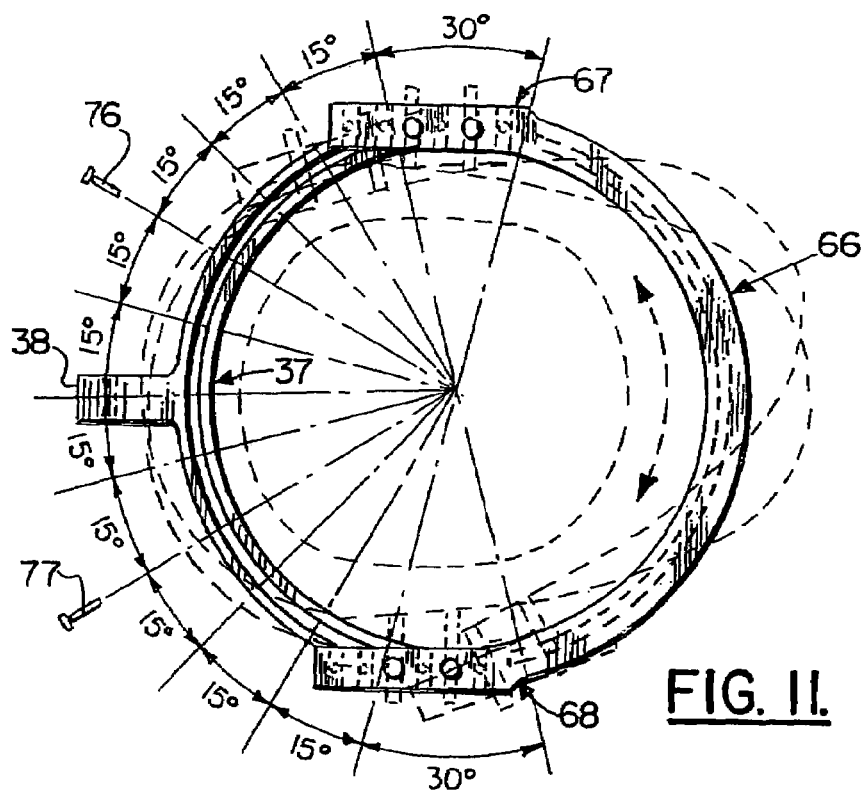
FIG. 11 is a top view of the rotational arc assembly of FIG. 1 indicating the rotational settings achievable by the preferred embodiment of FIG. 1.

As illustrated in FIGS. 9-10, the occipital-mandible support member 78 includes a left section 79 and a right section 80 preferably molded from a thermoset plastic or resin to form a rigid structure shaped to form a front cup-shaped section 81 in which the patient chin 82 can be positioned. Sections 79 and 80 when joined are also shaped to form a rear upward and outward curved section 83 that surrounds the upper back portion 84 of the patient neck and occipital portion 84A of the patient head. Each section 79 and 80 is provided with a rigid side plate 85 having pins 86 and 87 extending horizontally therefrom. Alternatively, pins 86 and 87 can be rectangular locking bars extending from ridge side plate 85. Each pin 86 and 87, or alternatively, each rectangular locking bar, is provided with a series of vertically extending openings 88 that permit each locking pins 89 and 90 to be inserted through openings 88 and vertical openings 73 of locking bars 67 and 68, respectively. If rectangular locking bars are used, then openings 74 would be replaced with a single horizontal extending slot shaped opening wherein the locking bars could slide forward, backward, and laterally in the slot shaped opening the more easily fit mandible supports 79 and 80 to the patient.

Left and right sections 79 and 80 are attached to one another utilizing known attaching means such as hook and loop fasteners 91 and 92 or other known devices such as latches, cinches, straps, snaps, etc. If desired, sections 79 and 80 can be constructed with hinges to facilitate donning and removal of the sections. In a more preferred embodiment, as illustrated in FIG. 4, left and right sections 79 and 80 will have inner cushioning pads 93 and 94, respectively, to prevent chaffing and provide comfort to the patient while wearing the device 1. In an alternate embodiment left and right occipital-mandible support sections 79 and 80 can be constructed without forming the front cup-shaped section 81.

In rehabilitation of cervical or cervicothoracic spinal injuries, patients' treating physicians and physical therapists evaluate factors determining whether rotational range therapy is indicated; said factors include, but are not limited to type, location, and severity of the injury; stabilization of the spine, and range of motion without pain.

When rotational range therapy is indicated, patients' physician or physical therapist chooses the appropriate initial maximum degree of active rotation and schedule of progressive increases in maximum active rotation according to the needs of the individual patient. Factors to consider when increasing rotational range include, but are not limited to, range of motion without pain, stabilization of the spinal column and associated connective tissues, vertebral disc protrusion or herniation, nerve root impingement, and strength of the neck muscles. Physicians and physical therapists monitor said factors in treating patients with the present invention and method to increase cervical muscle strength and rotational range of the head. Between rotational therapy treatments to increase rotational range, the present invention is adjustable to a smaller rotational range functioning as a rotational range cervical brace to maintain gains in rotational range and further strengthen the cervical muscles. In a preferred embodiment illustrated in FIG. 5 springs 95 may be inserted in one or both channels 49. In this embodiment the patent is alerted when the predetermined range of motion has almost been completed so as to reduce risk of injury when the full range of motion has been completed. Also by varying the compression characteristics of springs 95 a resistive force is achieved that can be used to strengthen the neck muscles. In that embodiment pins 76 and 77 lock springs 95 in channels 49. The anterior end 96 of spring 95 pins 76, 77 contact that engages the ends of rotational member 65 to cushion the end of travel of rotational member 65.

Thus, the present invention achieves the object of facilitating a method of cervical therapy where the load of the head is transferred to the shoulders/upper chest and the head and neck actively rotate in progressively extensive ranges of horizontal rotation without tilting the head.

The present invention also functions as a rotational range cervical brace for patients with weakened neck muscles from neuromuscular diseases. The present invention comfortably supports the load of the head allowing patients to rotate their heads.

Once fitted to a patient, the present invention can be easily donned and removed in three assemblies. The present invention is removed by first releasing the hook and loop fastener 92 connecting the left occipital-mandible section 79 and right occipital-mandible section 80. The bilateral latches 55 and 56 connecting the anterior section 36 and posterior section 37 are then detached. The anterior section 36 and the adjoined rotational member 65 and occipital-mandible support member 78 are then pulled forward to separate from the posterior section 37. The bilateral hook and loop fasteners 17-20 connecting the rear neck plate 11 and the front neck-sternum plate 12 and are then detached to separate and remove the rear neck plate 11 and the front neck-sternum plate 12. Donning the present invention once fitted is achieved by simply reversing the removal steps.

These preferred embodiments, as well as other obvious alternative embodiments are to be included within the scope of the invention as defined by the following claims.

What I claim is:

1. A cervical brace and therapy device for use to rehabilitate an injured neck of a person comprising:
   a. a base support structure shaped to fit about the neck and rest on the shoulders of the person;
   b. a support ring assembly having a track and at least two stop members variably positionable in the track; the support ring assembly attachable to the base support structure in a horizontal position below the mandible of the person, the support ring assembly having an anterior section and a posterior section;
   c. a rotational member having a member shaped to operatively mate with the track of the support ring assembly in a manner to rotate about the support ring assembly; wherein the at least two stop members are affixable in at least two or more positions in the track to limit the rotational range of the rotational member about the support ring assembly to a variably pre-determined rotational range;
   d. an occipital-mandible support member shaped to accommodate the mandible and the occipital portions of the head of the person, the occipital-mandible support member being attachable to the rotational member in a manner to permit the occipital-mandible support member a predetermined range of rotation; and
   e. wherein the occipital-mandible support member is configured to provide a degree of motion of 0 degrees and 210 degrees, and at least one other mechanically restricted user-selectable degree of motion in-between; and
   f. a cushioning assembly variably positionable in the track, wherein the cushioning assembly is positioned anterior to a desired stop member affixed in the track at a user-selected position such that the stop member limits the rotational range of the rotational member, wherein the cushioning assembly cushions against the direct contact of the rotational member with the stop member, when the rotational member reaches the end of the pre-determined rotational range.

2. A cervical brace and therapy device according to claim 1 wherein the base support structure comprises a rear neck contoured plate and a front contoured plate affixable to one another.

3. A cervical brace and therapy device according to claim 2 wherein at least one of the plates having openings to reduce the weight of the base support structure, better ventilate heat generated by the body positioned beneath the base support structure, and increase wearing comfort.

4. A cervical brace and therapy device according to claim 1 wherein the support ring assembly is attachable to the base support structure at two or more places.

5. A cervical brace and therapy device according to claim 1 wherein the base support structure comprises a neck-sternum section and a neck-upper back section attachable to one another along their edges by of a hook and loop fastener, latches, snaps, cinches, or a combination thereof, and shaped when joined to rest on the upper back, shoulders and sternum of the person.

6. A cervical brace and therapy device according to claim 5 wherein the neck-sternum section and the neck-upper back section each have a rigid outer shell and a cushioning inner liner positioned to contact the person.

7. A cervical brace and therapy device according to claim 6 wherein the liner is attachable by one or more hook and loop fasteners.

8. A cervical brace and therapy device according to claim 5 wherein the neck-upper back section further comprises a first vertically extending hollow tubular member for receiving one end of a first vertical positioning shaft extending vertically downward from the posterior section of the support ring assembly.

9. A cervical brace and therapy device according to claim 8 wherein the first vertically extending hollow tubular member and the first vertical positioning shaft are each provided with a series of opening extending there through sized and positioned to permit the insertion of a locking pin through aligned openings of the first vertically extending hollow tubular member and the first vertical positioning shaft.

10. A cervical brace and therapy device according to claim 9 wherein the cross-sectional shape of the vertically extending tubular member is shaped having two or more sides and the cross-sectional shape of the vertical positioning shaft is of similar smaller shape to permit the first vertical positioning shaft to extend into the first vertically extending hollow tubular member.

11. A cervical brace and therapy device according to claim 5 wherein the neck-sternum section further comprises a second vertical, upward extending hollow tubular member for receiving one end of a second vertical positioning shaft extending vertically downward from the anterior section of the support ring assembly.

12. A cervical brace and therapy device according to claim 11 wherein the second vertically extending hollow tubular member and the second vertical positioning shaft are each provided with a series of opening extending there through sized and positioned to permit the insertion of a locking pin through aligned openings of the second vertically extending hollow tubular member and the second vertical positioning shaft.

13. A cervical brace and therapy device according to claim 1 wherein the anterior section and the posterior section of the support ring assembly are affixable to one another to form a ring sized to fit about the neck of the person, each having a top surface provided with a track to which the rotational member is attached to permit the rotational member to move around the track.

14. A cervical brace and therapy device according to claim 1, wherein the cushioning assembly comprises a yield member and a cushioning member, wherein the yield member and the cushioning member are affixed in the track anterior to the desired stop member, wherein the cushioning member is positioned between the stop member and the yield member, wherein the yield member has two ends, wherein at one end, the yield member is to be engaged by the rotational member, wherein at the other end, the yield member is affixed to the cushioning member, such that when the rotational member approaches the stop member near the end of the predetermined range of motion, the rotational member engages the yield member, whereby the yield member is pushed against the cushioning member, wherein the cushioning member checks the movement of the yield member and the rotational member towards the stop member.

15. A cervical brace and therapy device according to claim 14, wherein the cushioning member comprises a spring, wherein the spring is configured to be compressed when the yield member is pushed against it.

16. A cervical brace and therapy device for use to rehabilitate an injured neck of a person comprising:
  a. a base support structure shaped to fit about the neck and rest on the shoulders of the person; the base support structure comprising a neck-sternum section and a neck-upper back section attachable to one another along their edges by a securing means and shaped when joined to rest on the upper back, shoulders and sternum of the person; wherein the neck-sternum section further comprises a second vertical, upward extending hollow tubular member for receiving one end of a second vertical positioning shaft extending vertically downward from the anterior section of the support ring assembly; the second vertically extending hollow tubular member and the second vertical positioning shaft are each provided with a series of openings extending there through sized and positioned to permit the insertion of a locking pin through aligned openings of the second vertically extending hollow tubular members and the second vertical positioning shaft;
  b. a support ring assembly attachable to the base support structure in a horizontal position below the mandible of the person, the support ring assembly having an anterior section and a posterior section; the posterior section of the support ring assembly having a series of horizontally positioned openings spaced apart a known distance and extending through the track;
  c. a rotational member having opposing ends and attached to the support ring assembly in a manner to rotate about the support ring assembly; each of the opposing ends of the rotational member are provided with a first series of vertical openings extending through the rotational member and a second series of horizontal openings extending through the rotational member;
  d. an occipital-mandible support member shaped to accommodate the mandible and the occipital portions of the head of the person, the occipital-mandible support member being attachable to the rotational member in a manner to permit the occipital-mandible support member a predetermined range of motion; and
  wherein the occipital-mandible support member is configured to provide a degree of motion of between about 0 degrees and 210 degrees, and at least one other user-selectable degree of motion in-between; the occipital-mandible support member having opposing pairs of horizontally extending pins sized and positioned to extend through corresponding openings in the second series of horizontal openings of the rotational member, the pins having a series of vertical openings extending through the pins; a first set of locking pins extendable through the aligned openings formed by one of the vertical openings in the occipital-mandible support member pin and one of the vertical openings in the rotational member; and a second set of locking pins extendable through the horizontal openings in the posterior section of the support ring assembly corresponding to a predetermined range of rotation, and
  e. a cushioning assembly variably positionable in the track, wherein the cushioning assembly is positioned anterior to a desired locking pin that extends through a user-selected horizontal opening in the track corresponding to a predetermined range of motion, such that the locking pin limits the rotational range of the rotational member, wherein the cushioning assembly cushions against the direct contact of the rotational member with the locking pin, when the rotational member nears the end of the pre-determined rotational range.

17. A cervical brace and therapy device according to claim 16, wherein the cushioning member comprises a spring, wherein the spring is configured to be compressed when the yield member is pushed against it.

18. A structure for use with a cervical brace and therapy device to control the degree of active head rotation without permitting the tilting of the head the improvement to which comprising:
   a. a support ring assembly having a track about the support ring assembly; the track provided with two or more stop members variably positionable on the track to variably restrict the range of rotation of the rotational member about the support ring assembly to a predetermined range of rotation;
   b. a rotational member having a member shaped to operatively mate with the track of the support ring assembly in a manner to permit the rotational member to rotate about the support ring assembly within the predetermined range of rotation; and
   c. an occipital-mandible support member shaped to accommodate the mandible and the occipital portions of the head of the person, the occipital-mandible support member being attachable to the rotational member in a manner to permit the occipital-mandible support member the predetermined range of rotation; and
   d. wherein the occipital-mandible support member is configured to provide the pre-determined range of rotation of between about 0 degrees and 210 degrees, and at least one other user-selectable degree of motion in between, as determined by the position of the stop members.

19. A structure according to claim 18 wherein the anterior section and the posterior section of the support ring assembly are attachable to one another to form a ring sized to fit about the neck of the person, each having a top surface provided with a track to which the rotational member is attached to permit the rotational member to move around the track.

20. A structure according to claim 19 wherein:
   a. each of the opposing ends of the rotational member are provided with a first series of vertical openings extending through the rotational member and a second series of horizontal openings extending through the rotational member;
   b. the occipital-mandible support member having opposing pairs of horizontally extending pins sized and positioned to extend through corresponding openings in the second series of horizontal openings of the rotational member, the pins having a series of vertical openings extending through the pins;
   c. the posterior section of the support ring assembly having a series of horizontally positioned openings spaced apart a known distance and extending through the track;
   d. a first set of locking pins extendable through the aligned openings formed by one of the openings in the occipital-mandible support member pin and one of the vertical openings in the rotational member; and
   e. a second set of locking pins extendable through the aligned horizontal openings in the posterior section of the support ring assembly to limit movement of the rotational member to a predetermined range of rotation.

21. A structure according to claim 20 further comprising a third set of locking pins extendable through the aligned horizontal openings of the anterior section of the support ring assembly to prevent movement of the rotational member.

22. A cervical brace and therapy device according to claim 20, further comprising a cushioning assembly variably positionable in the track, wherein the cushioning assembly is positioned anterior to a desired locking pin that extends through a user-selected horizontal opening in the track corresponding to a predetermined range of motion, such that the locking pin limits the rotational range of the rotational member, wherein the cushioning assembly cushions against the direct contact of the rotational member with the locking pin, when the rotational member reaches the end of the pre-determined rotational range.

23. A cervical brace and therapy device according to claim 22, wherein the cushioning assembly comprises a hollow housing affixed within the track of the support ring assembly, anterior to the user-selected horizontal opening extending through the track and corresponding to a desired predetermined range of motion, wherein the housing further comprises a first open end and a second open end, and a cushioning member running the length of the housing from the first end to the second end, wherein the housing further comprises a horizontal opening extending through housing, this horizontal opening in the housing in alignment with the user-selected horizontal opening in the track corresponding to a desired predetermined range of motion, wherein the housing is affixed within the track by the locking pin extending through the aligned openings formed by the user-selected horizontal opening in the track and the horizontal opening in the housing, wherein the housing further comprises a yield member situated at the second end of the housing, wherein the yield member has two ends, wherein the yield member is affixed to the cushioning member at one end, and wherein at the other end, a portion of the yield member extends outwardly from the second open-end of the housing to be engaged by the rotational member, such that when the rotational member approaches the locking pin and nears the end of the pre-determined range of motion, the rotational member engages the yield member at the outwardly extending portion of the yield member, such that this portion of the yield member is pushed inwardly toward the housing and against the cushioning member, whereby the cushioning member checks the movement of the yield member and the rotational member towards the locking pin.

24. A cervical brace and therapy device according to claim 23, wherein the cushioning member comprises a spring, wherein the spring is configured to be compressed when the yield member is pushed against it.

25. A method of cervical therapy on a person having a head, back side of a lower neck, an upper back, a lower throat, an upper chest and shoulders that transfers the load of the patient head to the patient shoulders while permitting a limited range of horizontal head rotation, which method comprises:
   a. positioning a base support structure on the shoulders;
   b. affixing to the base support member at a position below the patient mandible a support ring having a track and having a rotational member comprising a member shaped to operatively mate with the guide member to permit the rotational member to rotate about the support ring; at least two stop members variably affixable in at least two or more positions to the track to limit the rotational range of the rotational member about support ring to a predetermined rotational range;
   and operatively attached to the support ring to provide a predetermined range of horizontal head rotation;

c. affixing an occipital-mandible support member to the rotational member and about the patient occipital and mandible at a position that supports the patient head at a desired horizontal position;
d. rotating the patient head within in the predetermined rotational range of horizontal head movement for a desired period of time; and
e. wherein the stop members are positionable in the track to selectively limit the predetermined rotational motion between about 0 degrees and 210 degrees of the rotational member relative to the support ring.

26. A method according to claim 25 further comprising:
a. adjusting the position of the stop members in the track to permit a second predetermined range of horizontal head rotation; and
b. rotating the patient head within the predetermined second range of horizontal head movement.

27. A method according to claim 25 further comprising periodic adjusting of the stop members to permit increasingly greater range of horizontal head rotation.

28. A method according to claim 25 wherein positioning the base support structure on the back side of the patient lower neck, the patient upper back, the patient lower throat, the patient upper chest, and the patient shoulder in a manner to permit the base support structure to transfer the load of the patient head to the patient shoulders.

* * * * *